(12) United States Patent
Adams et al.

(10) Patent No.: US 7,698,268 B1
(45) Date of Patent: Apr. 13, 2010

(54) METHOD AND SYSTEM FOR FILTERING FALSE POSITIVES

(75) Inventors: Norm Adams, Cave Creek, AZ (US); Scott Ellard, Marietta, GA (US); Scott Schumacher, Northridge, CA (US)

(73) Assignee: Initiate Systems, Inc., Chicago, IL (US)

( * ) Notice: Subject to any disclaimer, the term of this patent is extended or adjusted under 35 U.S.C. 154(b) by 126 days.

(21) Appl. No.: 11/521,946

(22) Filed: Sep. 15, 2006

(51) Int. Cl.
*G06F 7/00* (2006.01)
*G06F 17/30* (2006.01)
*G06F 17/00* (2006.01)
*A61F 5/00* (2006.01)
*G06F 19/00* (2006.01)

(52) U.S. Cl. .................................. 707/5; 707/102; 705/3
(58) Field of Classification Search ........................ None
See application file for complete search history.

(56) References Cited

U.S. PATENT DOCUMENTS

| 5,497,486 | A | | 3/1996 | Stolfo | |
|---|---|---|---|---|---|
| 5,991,758 | A | | 11/1999 | Ellard | |
| 5,999,937 | A | | 12/1999 | Ellard | |
| 2002/0073099 | A1 | * | 6/2002 | Gilbert et al. | 707/104.1 |
| 2005/0154615 | A1 | * | 7/2005 | Rotter et al. | 705/3 |
| 2005/0256740 | A1 | * | 11/2005 | Kohan et al. | 705/2 |
| 2007/0299697 | A1 | * | 12/2007 | Friedlander et al. | 705/3 |
| 2008/0005106 | A1 | * | 1/2008 | Schumacher et al. | 707/6 |
| 2008/0126160 | A1 | * | 5/2008 | Takuechi et al. | 705/7 |

OTHER PUBLICATIONS

Hamming Distance, HTML. wikipedia.org, Available: http://en.wikipedia.org/wiki/Hamming_distance (as of May 8, 2008).*
Fruend et al, Statistical Methods, 1993, Academic Press Inc, United Kingdom Edition, pp. 112-117.*
Original Paper: "Record Linkage in the National Dose Registry of Canada" by M.E. Fair., pp. S37-S43.

* cited by examiner

*Primary Examiner*—Pierre M Vital
*Assistant Examiner*—Jason Liao
(74) *Attorney, Agent, or Firm*—Sprinkle IP Law Group

(57) ABSTRACT

Embodiments of the present invention may be used in the generation of an overall weight from the comparison of various attributes of data records, where the linking of the data records is dependent on the overall weight. More specifically, embodiments of the present invention may calculate a false positive penalty based on a set of results, each of the set of results based on a comparison of an attribute. The false positive penalty may be subtracted from the overall weight generated from the comparison of the attributes of data records to adjust the overall weight. By configuring which attributes of the data records are used as the set of attributes for generating the false positive penalty, and the penalties associated with a particular combination of results for the comparisons of these attributes, the incidence of false positives in the linking of data records may be significantly reduced.

19 Claims, 4 Drawing Sheets

| DIM 1 INDEX | NAME RESULT | GENDER RESULT |
|---|---|---|
| 0 | MISSING | MISSING |
| 1 | EXACT | MISSING |
| 2 | PARTIAL | MISSING |
| 3 | DISAGREE | MISSING |
| 4 | MISSING | AGREE |
| 5 | EXACT | AGREE |
| 6 | PARTIAL | AGREE |
| 7 | DISAGREE | AGREE |
| 8 | MISSING | DISAGREE |
| 9 | EXACT | DISAGREE |
| 10 | PARTIAL | DISAGREE |
| 11 | DISAGREE | DISAGREE |

|  | NAME | GENDER | SSN | DOB | BIRTH YEAR DIFF. | BIRTH DATE EDIT DIST |
|---|---|---|---|---|---|---|
| FIRST PERMUTATION | PARTIAL | DISAGREE |  |  |  |  |
| SECOND PERMUTATION |  | DISAGREE |  | DISAGREE |  |  |
| THIRD PERMUTATION |  | DISAGREE | DISAGREE |  |  |  |
| FOURTH AND FIFTH PERMUTATIONS | DISAGREE OR PARTIAL |  |  | DISAGREE |  |  |
| FIFTH AND SIXTH PERMUTATIONS | DISAGREE OR PARTIAL |  | DISAGREE |  |  |  |
| SEVENTH PERMUTATION |  |  |  |  | >15 YEARS | >1 |
| EIGHTH PERMUTATION |  |  | DISAGREE | DISAGREE |  |  |

*FIG. 6*

METHOD AND SYSTEM FOR FILTERING FALSE POSITIVES

TECHNICAL FIELD OF THE INVENTION

This invention relates generally to associating data records, and in particular to identifying data records that may contain information about the same entity such that these data records may be associated. Even more particularly, this invention relates to the statistical identification of data records for association.

BACKGROUND OF THE INVENTION

In today's day and age, the vast majority of businesses retain extensive amounts of data regarding various aspects of their operations, such as inventories, customers, products, etc. Data about entities, such as people, products, parts or anything else may be stored in digital format in a data store such as a computer database. These computer databases permit the data about an entity to be accessed rapidly and permit the data to be cross-referenced to other relevant pieces of data about the same entity. The databases also permit a person to query the database to find data records pertaining to a particular entity, such that data records from various data stores pertaining to the same entity may be associated with one another.

A data store, however, has several limitations which may limit the ability to find the correct data about an entity within the data store. The actual data within the data store is only as accurate as the person who entered the data, or an original data source. Thus, a mistake in the entry of the data into the data store may cause a search for data about an entity in the database to miss relevant data about the entity because, for example, a last name of a person was misspelled or a social security number was entered incorrectly, etc. A whole host of these types of problems may be imagined: two separate record for an entity that already has a record within the database may be created such that several data records may contain information about the same entity, but, for example, the names or identification numbers contained in the two data records may be different so that it may be difficult to associate the data records referring to the same entity with one other.

For a business that operates one or more data stores containing a large number of data records, the ability to locate relevant information about a particular entity within and among the respective databases is very important, but not easily obtained. Once again, any mistake in the entry of data (including without limitation the creation of more than one data record for the same entity) at any information source may cause relevant data to be missed when the data for a particular entity is searched for in the database. In addition, in cases involving multiple information sources, each of the information sources may have slightly different data syntax or formats which may further complicate the process of finding data among the databases. An example of the need to properly identify an entity referred to in a data record and to locate all data records relating to an entity in the health care field is one in which a number of different hospitals associated with a particular health care organization may have one or more information sources containing information about their patient, and a health care organization collects the information from each of the hospitals into a master database. It is necessary to link data records from all of the information sources pertaining to the same patient to enable searching for information for a particular patient in all of the hospital records.

There are several problems which limit the ability to find all of the relevant data about an entity in such a database. Multiple data records may exist for a particular entity as a result of separate data records received from one or more information sources, which leads to a problem that can be called data fragmentation. In the case of data fragmentation, a query of the master database may not retrieve all of the relevant information about a particular entity. In addition, as described above, the query may miss some relevant information about an entity due to a typographical error made during data entry, which leads to the problem of data inaccessibility. In addition, a large database may contain data records which appear to be identical, such as a plurality of records for people with the last name of Smith and the first name of Jim. A query of the database will retrieve all of these data records and a person who made the query to the database may often choose, at random, one of the data records retrieved which may be the wrong data record. The person may not often typically attempt to determine which of the records is appropriate. This can lead to the data records for the wrong entity being retrieved even when the correct data records are available. These problems limit the ability to locate the information for a particular entity within the database.

To reduce the amount of data that must be reviewed, and prevent the user from picking the wrong data record, it is also desirable to identify and associate data records from the various information sources that may contain information about the same entity. There are conventional systems that locate duplicate data records within a database and delete those duplicate data records, but these systems may only locate data records which are substantially identical to each other. Thus, these conventional systems cannot determine if two data records, with, for example, slightly different last names, nevertheless contain information about the same entity. In addition, these conventional systems do not attempt to index data records from a plurality of different information sources, locate data records within the one or more information sources containing information about the same entity, and link those data records together. Consequently, it would be desirable to be able to associate data records from a plurality of information sources which pertain to the same entity, despite discrepancies between attributes of these data records.

No matter the system utilized to identify and associate data records, however, certain conditions may arise with respect to associating these data records. More specifically, there will almost certainly be cases where data records which should be associated are not (known as false negative) and cases where data records are associated when they do not refer to the same entity (known as a false positive). In certain areas, these conditions may be relatively innocuous, the false negatives and false positives are easily dealt with and no harm may arise. In highly critical areas such as health care industries, however, these conditions may have the potential to cause great harm. This is particularly true for false positives. Mistakenly associating data records which refer to distinct entities may have large ramifications when it comes to the application of medical care and pharmaceuticals.

Thus, there is a need for system and methods for comparing attributes of data records and linking these data records which is operable to filter these linked data records for false positives, and it is to this end that embodiments of the present invention are directed.

SUMMARY OF THE INVENTION

Embodiments of systems and methods for reducing false positives during the linking of data records are disclosed herein. Broadly speaking, embodiments of the present invention may be used in the generation of an overall weight from the comparison of various attributes of data records, where the linking of the data records is dependent on the overall weight. More specifically, embodiments of the present invention may provide a set of code (e.g., a computer program product comprising a set of computer instructions stored on a computer readable medium and executable or translatable by a computer processor) translatable to calculate a false positive penalty based on a set of results, each of the set of results based on a comparison of an attribute. The false positive penalty may be subtracted from the overall weight generated from the comparison of the attributes of data records to adjust the overall weight. By configuring which attributes of the data records are used as the set of attributes for generating the false positive penalty, and the penalties associated with a particular combination of results for the comparisons of these attributes, the incidence of false positives in the linking of data records may be significantly reduced.

In one embodiment, a comparison between attributes from two data records yields a set of results which are, in turn, used to generate a false positive penalty. The overall weight which was determined for the two data records may then be adjusted using this false positive penalty.

In some embodiments, the set of results to utilize in determining a false positive penalty may be configured.

In other embodiments, the attributes utilized to generate the false positive penalty may be the attributes used to determine the overall weight for the two records, or a subset thereof.

In still other embodiments, the false positive penalty to be utilized in conjunction with any particular set of results may be configured.

Embodiments of the present invention may provide the technical advantage of more effective linking of data records through the reduction of the incidences of false positives when linking these data records. More specifically, embodiments of the present invention may prove effective at reducing the incidences of false positives when linking data records pertaining to people, especially when these data records undergoing comparison and linking may comprise members of the same family or the same name.

Other technical advantages of embodiments of the present invention include an almost endless degree of configurability and flexibility. In other words, the attributes, results, other parameters utilized in the determination of the false positive penalty to impose (if any) and the values for false positive penalties themselves may be configurable such that embodiments of the present invention may be fined tuned according to a wide variety of variables.

These, and other, aspects of the invention will be better appreciated and understood when considered in conjunction with the following description and the accompanying drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE DRAWINGS

The drawings accompanying and forming part of this specification are included to depict certain aspects of the invention. A clearer impression of the invention, and of the components and operation of systems provided with the invention, will become more readily apparent by referring to the exemplary, and therefore nonlimiting, embodiments illustrated in the drawings, wherein identical reference numerals designate the same components. Note that the features illustrated in the drawings are not necessarily drawn to scale.

FIG. 6 depicts one embodiment of various permutations for a set of results which may cause a false positive penalty to be imposed.

DETAILED DESCRIPTION

The invention and the various features and advantageous details thereof are explained more fully with reference to the nonlimiting embodiments that are illustrated in the accompanying drawings and detailed in the following description. Descriptions of well known starting materials, processing techniques, components and equipment are omitted so as not to unnecessarily obscure the invention in detail. Skilled artisans should understand, however, that the detailed description and the specific examples, while disclosing preferred embodiments of the invention, are given by way of illustration only and not by way of limitation. Various substitutions, modifications, additions or rearrangements within the scope of the underlying inventive concept(s) will become apparent to those skilled in the art after reading this disclosure.

Reference is now made in detail to the exemplary embodiments of the invention, examples of which are illustrated in the accompanying drawings. Wherever possible, the same reference numbers will be used throughout the drawings to refer to the same or like parts (elements).

Figure 1:
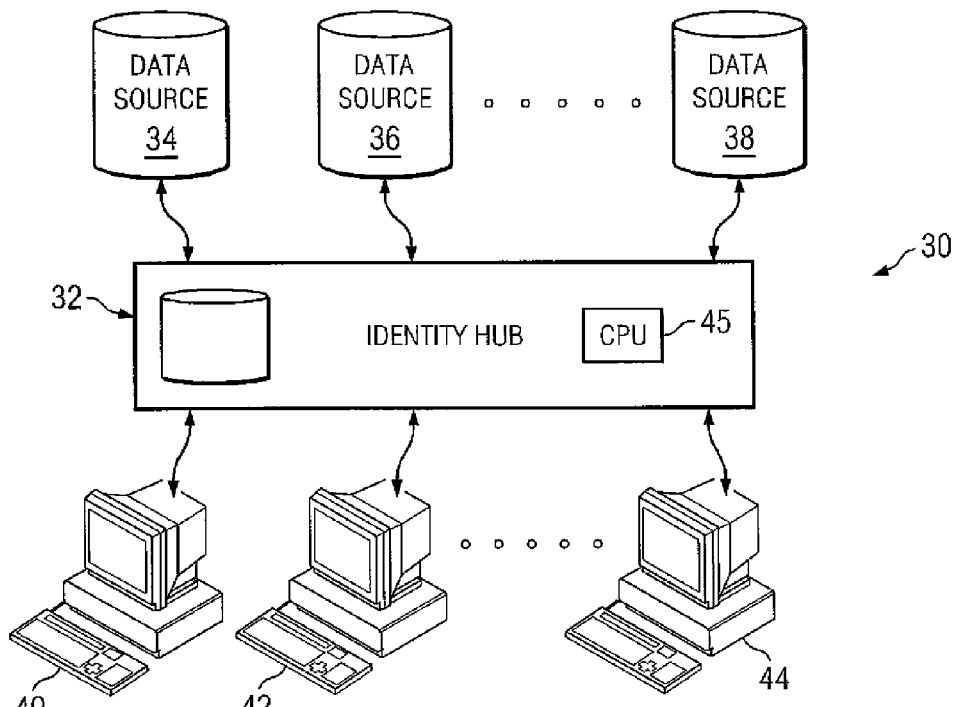
FIG. 1 depicts one embodiment of an example infrastructure.

Before turning to embodiments of the present invention, a general description of an example infrastructure or context which may be helpful in explaining these various embodiments will be described. A block diagram of one embodiment of just such an example infrastructure is described in FIG. 1. FIG. 1 is a block diagram illustrating one embodiment of an entity processing system 30 in accordance with embodiments of the invention. The entity processing system 30 may include an identity hub 32 that processes, updates or stores data pertaining to data records about one or more entities from one or more data sources 34, 36, 38 and responds to commands or queries from a plurality of operators 40, 42, 44, where the operators may be either users or information systems. The identity hub 32 may operate with data records from a single information source or, as shown, data records from multiple information sources. The entities tracked using the identity hub 32 may include for example, patients in a hospital, participants in a health care system, parts in a warehouse or any other entity that may have data records and information contained in data records associated with it. The identity hub 32 may be one or more computer systems with a central processing unit 45 executing computer readable instructions (e.g. a software application) that performs the function of the identity hub 32. The identity hub 32 may also be implemented using hardware circuitry.

As shown, the identity hub 32 may receive data records from the data sources 34, 36, 38 as well as write corrected data back into the information sources 34, 36, 38. The corrected data communicated to the data sources 34, 36, 38 may include information that was correct, but has changed, information about fixing information in a data record or information about links between data records.

In addition, one of the operators 40, 42, 44 may transmit a query to the identity hub 32 and receive a response to the query back from the identity hub 32. The one or more data sources 34, 36, 38 may be, for example, different databases that possibly have data records about the same entities. For example, in the health care field, each information source 34, 36, 38 may be associated with a particular hospital in a health care organization and the health care organization may use the identity hub 32 to relate the data records associated with the plurality of hospitals so that a data record for a patient in Los Angeles may be located when that same patient is on vacation and enters a hospital in New York. The identity hub 32 may be located at a central location and the data sources 34, 36, 38 and users 40, 42, 44 may be located remotely from the identity hub 32 and may be connected to the identity hub 32 by, for example, a communications link, such as the Internet or any other type communications network, such as a wide area network, intranet, wireless network, leased network, etc.

The identity hub 32 may have its own database that stores complete data records in the identity hub, or alternatively, the identity hub may also only contain sufficient data to identify a data record (e.g., an address in a particular data source 34, 36, 38) or any portion of the data fields that comprise a complete data record so that the identity hub 32 can retrieve the entire data record from the data source 34, 36, 38 when needed. The identity hub 32 may link data records together containing information about the same entity utilizing an entity identifier or an associative database separate from actual data records. Thus, the identity hub 32 may maintain links between data records in one or more data sources 34, 36, 38, but does not necessarily maintain a single uniform data record for an entity.

More specifically, the identity hub may link data records in data sources 34, 36, 38 by comparing a data record (received from an operator, or from a data source 34, 36, 38) with other data records in data sources 34, 36, 38 to identify data records which should be linked together. This identification process may entail a comparison of one or more of the attributes of the data records with like attributes of the other data records. For example, a name attribute associated with one record may be compared with the name of other data records, social security number may be compared with the social security number of another record, etc. In this manner, data records which should be linked may be identified.

It will be apparent to those of ordinary skill in the art, that both the data sources 34, 36, 38 and the operators 40, 42, 44 may be affiliated with similar or different organizations or owners. For example, data source 34 may be affiliated with a hospital in Los Angeles run by one health care network, while data source 36 may be affiliated with a hospital in New York run by another health care network. Thus, the data records of each of data sources may be of a different format.

Figure 2A:
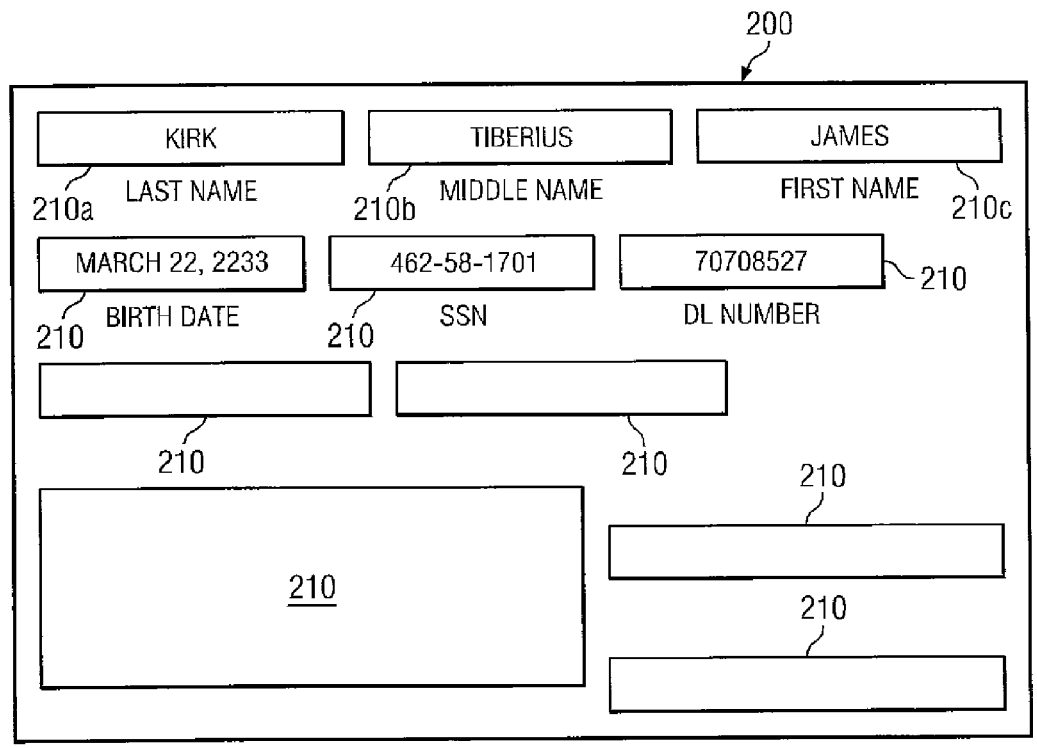
FIGS. 2A and 2B depict a representation of two embodiments of data records.
Figure 2B:
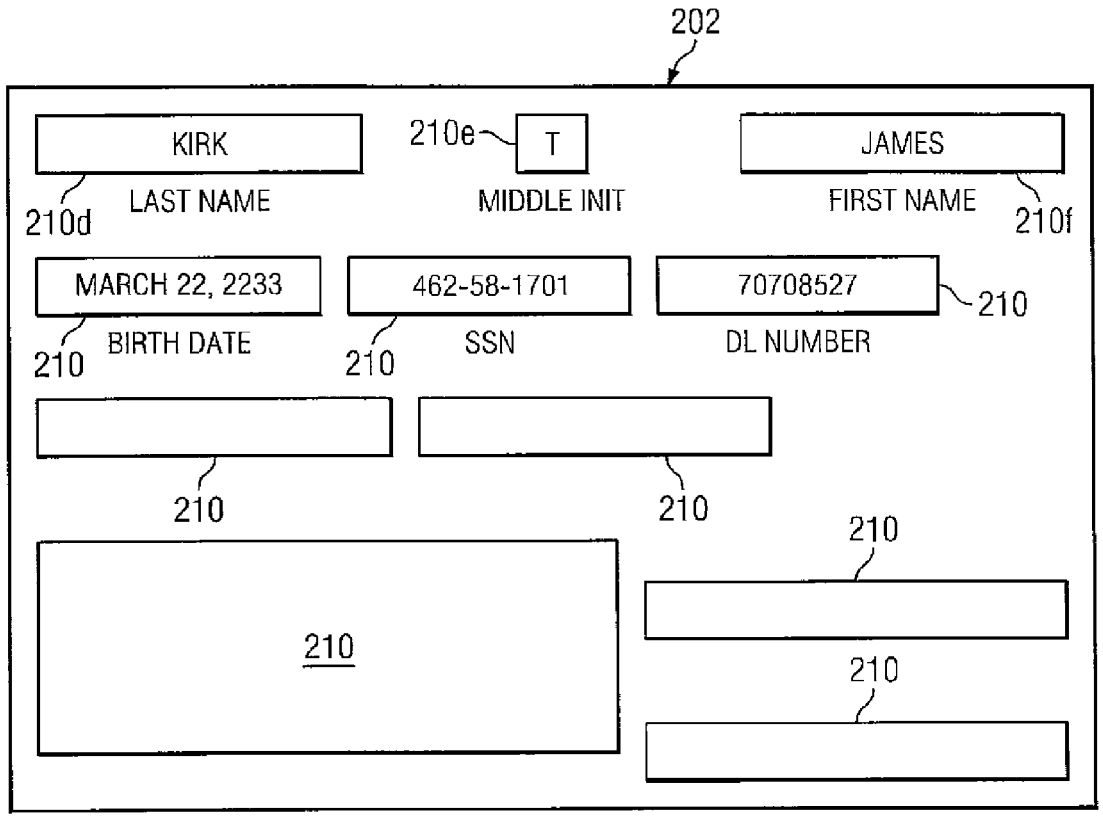

This may be illustrated more clearly with reference to FIGS. 2A and 2B, depicting two embodiments of example data records. Each of these data records 200, 202 has a set of fields 210 corresponding to a set of attributes of each of the data records. For example, one of the attributes of each of the records 200 may be a name, another attribute may be a social security number, birth date, gender, etc. It will be apparent that an attribute may comprise multiple fields 210 of a data record 200, 202, for example, the name attribute of data record 200 may comprise fields 210a, 210b and 210c, the last, middle and first name fields, respectively.

Notice, however, that each of the records may have a different format, for example data record 202 may have a filed for the attribute of driver's license number, while data record 200 may have no such field. Similarly, like attributes may have different formats as well. For example, name fields 210a, 210b 210c in record 200 may accept the entry of a full first, last and middle name, while name fields 210d, 210e, 210f in record 202 may be designed for full first and last names, but only allow the entry of a middle initial.

As may be imagined, discrepancies such as this may be problematic when comparing two or more data records (e.g. attributes of data records) to identify data records which should be linked. Complicating the linking of data records, information pertaining to the same entity may be incorrectly entered into a data record, or may change in one data record pertaining to the entity but not in another data record, etc.

Figure 3:
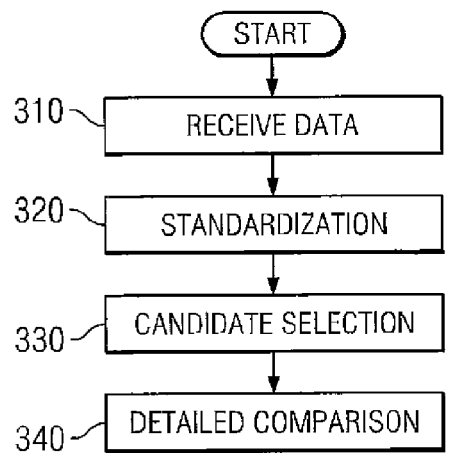
FIG. 3 depicts a flow diagram for one embodiment of comparing data records.

To deal with these possibilities, a system may be utilized which compares the various attributes of data records according to statistical algorithms to determine if data records refer to identical entities and hence, should be linked. To aid in an understanding of the systems and methods of the present invention it will be helpful to present an example embodiment of a methodology for identifying records pertaining to the same entity which may utilize these systems and methods. FIG. 3 depicts one such embodiment. A set of data records for comparison may be given for evaluation at step 310. These data records may include, for example, one or more new data records to compare to a set of existing data records (which may already exist in, for example, data sources 34, 36, 38 or which may be provided as well). At step 320 the data records for comparison may be standardized.

This standardization may comprise the standardization of attributes of a data record into a standard format, such that subsequent comparisons between like attributes of different data records may be performed according to this standard format. It will be apparent that each of the attributes of the data records to be compared may be standardized according to a different format, a different set of semantics or lexicon, etc.

Once the attributes of the data records to be compared have been standardized at step 320, a set of candidates may be selected to compare to the new data record at step 330. This candidate selection process may comprise a comparison of one or more attributes of the new data records to the existing data records to determine which of the existing new data records are similar enough to the new data records to entail further comparison. These candidates may then undergo a more detailed comparison to the new records where a set of attributes are compared between the records to determine if an existing data record should be linked or associated with the new data record. This more detailed comparison may entail comparing each of the set of attributes of one record (e.g. an existing record) to the corresponding attribute in the other record (e.g. the new record) to generate a weight for that attribute. The weights for the set of attributes may then be summed to generate an overall weight which can then be compared to a threshold to determine if the two records should be linked.

In some cases, however, data records which do not represent the same entity may be mistakenly linked. These false positives may occur for a variety of reasons. For example, family members may share a variety of characteristics which, in turn may lead to data records for different members of the same family being incorrectly linked (e.g. it may be incorrectly determined that these data records refer to the same person, and thus the data records linked). Typically, methods for reducing the occurrence of false positives take one or more attributes of the data records being compared and use a fixed penalty if there is a mismatch between any corresponding attribute in their respective data records (e.g. a mismatch penalty is imposed if there is a mismatch between the names in each data records. Because of this, these prior solutions were severely limited in both the combinations of attributes which could be utilized in filtering for false positives, and the final weight penalties that could be imposed for specific combinations of the results of the comparisons of these attributes. Consequently, it would be desirable to implement a false positive filter (e.g. algorithm) to help reduce the likelihood of incorrectly linking data record which associated with different entities, which can be configured to use various attributes which may be used in the linking of records and which may impose differing penalties based on different combinations of results for the evaluation of these attributes.

To that end, attention is now directed to systems and methods for reducing false positives during the linking of data records. Broadly speaking, embodiments of the present invention may be used in the generation of an overall weight from the comparison of various attributes of data records, where the linking of the data records is dependent on the overall weight. More specifically, embodiments of the present invention may calculate a false positive penalty based on a set of results each of the set of results based on a comparison of an attribute. The false positive penalty may be subtracted from the overall weight generated from the comparison of the attributes of data records to adjust the overall weight. By configuring which attributes of the data records are used as the set of attributes for generating the false positive penalty, and the penalties associated with a particular combination of results for the comparisons of these attributes, the incidence of false positives in the linking of data records may be significantly reduced.

Figures 4, 5:
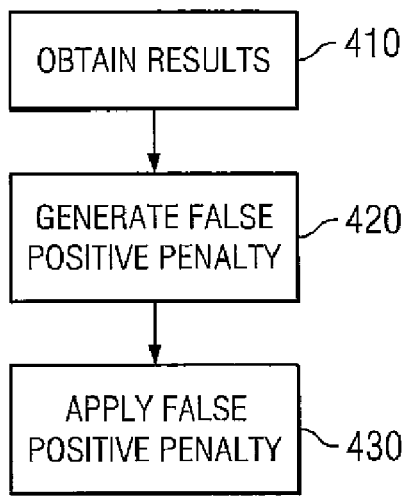
FIG. 4 depicts a flow diagram for one embodiment of determining a false positive penalty.
FIG. 5 depicts a table of values for index values corresponding to one embodiment of the present invention.

Turning now to FIG. 4, a flow diagram for one such embodiment of a method for generating a false positive penalty from the results of the comparisons of each of a set of attributes is depicted. More specifically, one or more attributes of a data record are compared with the corresponding attributes in another data records to generate a weight (e.g. step 340 of FIG. 3), data from the comparison of each of a set of these attributes may be obtained at step 410 (e.g. results), the combination of the results of these comparisons may then be used to generate a false positive penalty at step 420, after which the overall weight may be adjusted according to this false positive penalty at step 430. While embodiments of the present invention will be described in conjunction with a specific set of attributes, it will be understood that embodiments of the invention may be configurable to utilize any set or subset of attributes of data records or results corresponding to the comparison of these attributes, and that the specific penalties associated with any combination of these results may likewise be configurable and different penalties may be assigned for differing combinations results, a single penalty may be assigned for all combinations of results, a single penalty may be assigned for some, but not all, combinations of results, etc.

At step 410, then, the data resulting from the comparisons of a set of attributes may be obtained. The set of attributes or results utilized may be configured to include any set of attributes of the data records being compared, while the data resulting from the comparisons of the attributes may be configured to include the results of the comparison of the attributes or any tokens of the attributes, intermediary results used in the comparisons of attributes or the results of the comparisons of attributes obtained may be generated from comparisons of the attributes or parts of the attributes which were not used in the generation of an overall weight for the two data records.

In one embodiment, the set of attributes utilized may include name, gender, birth date and SSN. The results from the comparison of these attributes may be a name comparison which results in four values for the name comparison "equal"—where all the tokens of the names from each data record match exactly, "partial" if there is one or more initial or nickname/phonetic matches (as depicted in U.S. patent application Ser. No. 11/521,928 titled "Method and System For Comparing Attributes Such as Business Names" by Norm Adams et al filed on Sep. 15, 2006 and U.S. patent application Ser. No. 11/522,223, entitled "Method and System For Comparing Attributes Such as Personal Names" by Norm Adams et al and filed on Sep. 15, 2006 both of which are hereby fully incorporated herein by reference) between tokens of either of the names from either attribute and no mismatched between tokens, "different"—there is at least one token mismatch between the two names of the data records and "missing"— where one of the data records is missing name data or no comparison between name attributes was conducted during generation of a weight. It will be apparent that a numerical value may be assigned designating each of the results above.

Similarly, the results of a comparison of the values for the gender attribute of the two data record may be utilized with the three possible results being "agree", "disagree" or "missing"—where at least one of the data records does not have gender data or no comparison of the gender attributes was conducted during the generation of a weight. The results of comparisons of the values for the date of birth attribute of the two data record may also be utilized. One comparison may be the edit distance between the two dates of birth of the data records (e.g. a value of 1 for an edit distance of 1, value of 2 for edit distance of 2, etc.), while another comparison may be the difference in birth year. The difference in birth year may be represented by values, where 0 indicated that birth year data is missing or has not been compared, a value indicates a difference in birth year between 0 and 4 years, a value of 2 means the difference is between 5 and 9, etc. Edit distance between the social security numbers of the two records may also be utilized.

The results of the comparison of the various attributes obtained in step 410 may then be utilized to generate a false positive penalty in step 420. In one embodiment, the specific permutation of the set of results obtained from the comparison of the obtained at step 410 may be used to generate a false positive value. More specifically, in one embodiment, the combination of results obtained at step 410 may be used to access a data structure (e.g. index into a table, etc.) which may store a penalty value to be utilized based on that combination of results. In other words, the results of the comparisons may have an associated numeric value (e.g. "missing" for an attribute may have a value of 0, edit distance for an attribute may be a value of 1, etc.) and each of these numeric values may be used to index into a data structure to locate the false positive penalty associated with the particular permutation of results represented by those values. In one embodiment, a program (such as Python) may be used to generate data structures such as tables comprising false positive penalties for use with embodiments of the present invention.

In one particular embodiment, a four dimensional table may be utilized, with the first dimension of the table indexed by a value resulting from a combination of the result for the name comparisons and the result for the gender comparisons; the second dimension being the result of the edit distance comparisons between the date of birth attributes, the third dimension is the difference between the birth year of the two data records and the fourth dimension is the result of the edit distance comparisons between the SSNs of the two data records. For example, a certain false positive penalty corresponding to partial agreement on the name attribute between the two records, agreement of the gender attribute, an edit distance of one between the two date of birth attributes a difference of 20 or more on the year of birth and an edit distance of 3 between the two SSNs of the data records may correspond to entry (6,2,5,4) in the table. FIG. 5 depicts one embodiment of a table for the various numeric values of a first dimension of such a table based upon a combination of the values of result for the name comparisons and the result for the gender comparisons as discussed above.

Returning to FIG. 4, once a false positive penalty has been determined at step 420 the overall weight previously determined for the two data records via a comparison of one or more of their various attributes may be adjusted using this false positive penalty. The determination of whether to link the two data records can then be based on the overall weight which has been adjusted by this false positive penalty (e.g. does the overall weight exceed a threshold, etc.). By tuning the false positive penalty imposed according to a variety of factors, which may include sample data collected from one or more data sources 34, 36, 38, the attributes used to generate the penalty, the comparisons used in conjunction with those attributes, etc. In fact, the set of attributes, and the comparisons utilized in conjunction with each of these attributes used to generate a false positive penalty may be almost infinitely tunable according to a wide variety of factors.

It may be helpful here to depict an example of various permutations of the results of the comparisons of various attributes which may cause a false positive penalty to be applied. FIG. 6 depicts one example of embodiments of permutations of comparisons results for certain attributes. In this example, the comparison results utilized are name, gender, SSN, date of birth (DOB), birth year difference and birth date edit distance. A false positive penalty may be imposed if there is a partial agreement between the name attribute of two data records (e.g. initial, phonetic or nickname match) but the gender attributes of the two records disagree; if the gender attributes disagree and the bate of birth attributes disagree; if the gender attributes disagree and the SSN attributes disagree; if there is a disagreement or partial agreement between the name attribute and the date of birth attributes disagree; if there is a disagreement or partial agreement between the name attribute and the SSN attributes disagree; if the is a greater than a 15 year difference in the birth year attributes of the two data records, and the edit distance between the two birth dates of the two data records is greater than 1.

It will be noted, in conjunction with the above discussions, that each of these values for the results of the comparisons of the various attributes may have a numerical value associated with it, and these values may be used to index a table comprising values for the false positive penalty to be imposed for any permutation of values for the results of the comparisons of attributes. Thus, for the above example, the values associated with each of the permutations listed in FIG. 6 may serve to index an entry in a table with a positive value for a false positive penalty while the numerical values associated with any other permutations of the results of the comparisons of these attributes may serve to index into a table with a zero value for the false positive penalty. In this manner, a false positive penalty may be imposed for the example permutations only.

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component of any or all the claims.

What is claimed is:

1. A method for association of data records, comprising:

providing a system comprising an identity hub running an identity hub engine, the identity hub coupled to one or more external data sources through one or more networks, each external data source at a corresponding database;

receiving a first data record or a second data record from the one or more external data sources at the identity hub;

obtaining a first set of results, wherein each of the first set of results is a value generated based on a comparison between one of a first set of attributes from the first data record and the second data record, wherein the comparison between each of the first set of attributes is performed by the identity hub engine;

generating a first false positive penalty corresponding to the values of each of the first set of results to reduce the likelihood of the incorrect linking of the first data record and second data record, wherein the first false positive penalty is generated after the first set of results are obtained, the first false positive penalty is associated with the comparison of the first data record, generating the first positive penalty comprises determining the first false positive penalty utilizing the first set of result and generating the first false positive penalty is performed by the identity hub engine; and adjusting a first overall weight for a comparison between the first data record and the second data record using the first false positive penalty, wherein the first overall weight was determined utilizing the first set of results, the first overall weight is generated before it is adjusted, the adjusted first overall weight is utilized to determine if the first data record and the second data record should be linked and the adjustment of the first overall weight and the determining if the first data record and the second data record should be linked is performed by the identity hub engine.

2. The method of claim 1, wherein each of the first set of results corresponds to a numeric value and the set of numeric values are used to generate the false positive penalty.

3. The method of claim 2, wherein the set of numeric values are used as an index to a table comprising false positive penalties.

4. The method of claim 3, wherein the set of attributes include name, gender, date of birth and social security number.

5. The method of claim 4, wherein the set of results correspond to a name comparison, a gender comparison, an edit distance between the dates of birth, a difference in birth years and an edit distance between the social security numbers.

6. The method of claim 3, wherein obtaining the first set of results comprises configuring the first set of results to use.

7. The method of claim 3, further comprising configuring the first false positive penalty corresponding to the first set of results.

8. The method of claim 3, further comprising:
obtaining a second set of results, wherein each of the second set of results is based on a comparison between one of the first set of attributes from a third data record and a fourth data record, the second set of results differing from the first set of results, wherein obtaining the second set of results is performed by the identity hub engine;
generating a second false positive penalty based on the set of results, the second false positive penalty different from the first false positive penalty and corresponding to the comparison of the third data record and the fourth data record, wherein generating the second false positive penalty is performed by the identity hub engine; and
adjusting an second overall weight for a comparison between the third data record and the fourth data record using the second false positive penalty, wherein the second overall weight was determined utilizing each of the first set of attributes from the third data record and the fourth data record, wherein adjusting the second overall weight and the comparison between the third data record and the fourth data record are performed by the identity hub engine.

9. The method of claim 8, wherein the second false positive penalty is zero.

10. A computer readable storage media, comprising instructions translatable for implementing an identity hub engine on an identity hub the identity hub coupled to one or more external data sources through one or more networks, each external data source at a corresponding database the identity hub engine operable for:
receiving a first data record or a second data record from the one or more external data sources at the identity hub;
obtaining a first set of results, wherein each of the first set of results is a value generated based on a comparison between one of a first set of attributes from the first data record and the second data record;
generating a first false positive penalty corresponding to the values of each of the first set of results to reduce the likelihood of the incorrect linking of the first data record and second data record, wherein the first false positive penalty is generated after the first set of results are obtained, the first false positive penalty is associated with the comparison of the first data record and generating the first positive penalty comprises determining the first false positive penalty utilizing the first set of result; and
adjusting a first overall weight for a comparison between the first data record and the second data record using the first false positive penalty, wherein the first overall weight was determined utilizing the first set of results, the first overall weight is generated before it is adjusted and the adjusted first overall weight is utilized to determine if the first data record and the second data record should be linked.

11. The computer readable storage media of claim 10, wherein each of the first set of results corresponds to a numeric value and the set of numeric values are used to generate the false positive penalty.

12. The computer readable storage media of claim 11, wherein the set of numeric values are used as an index to a table comprising false positive penalties.

13. The computer readable storage media of claim 12, wherein the set of attributes include name, gender, date of birth and social security number.

14. The computer readable storage media of claim 13, wherein the set of results correspond to a name comparison, a gender comparison, an edit distance between the dates of birth, a difference in birth years and an edit distance between the social security numbers.

15. The computer readable storage media of claim 12, wherein obtaining the first set of results comprises configuring the first set of results to use.

16. The computer readable storage media of claim 12, the identity hub engine operable for configuring the first false positive penalty corresponding to the first set of results.

17. The computer readable storage media of claim 12, the identity hub engine operable for:
obtaining a second set of results, wherein each of the second set of results is based on a comparison between one of the first set of attributes from a third data record and a fourth data record, the second set of results differing from the first set of results;
generating a second false positive penalty based on the set of results, the second false positive penalty different from the first false positive penalty and corresponding to the comparison of the third data record and the fourth data record; and
adjusting an second overall weight for a comparison between the third data record and the fourth data record using the second false positive penalty, wherein the second overall weight was determined utilizing each of the first set of attributes from the third data record and the fourth data record.

18. The computer readable storage media of claim 17, wherein the second false positive penalty is zero.

19. A system for the linking of data records, comprising:
one or more data sources, each data source at a corresponding database; and
an identify hub linked to the one or more data sources through one or more networks, wherein the identity hub comprising a computer readable medium including instructions operable for implementing an identity hub engine for:
receiving a first data record or a second data record from the one or more data sources at the identity hub;
obtaining a first set of results, wherein each of the first set of results is a value generated based on a comparison between one of a first set of attributes from the first data record and the second data record;
generating a first false positive penalty corresponding to the values of each of the first set of results to reduce the likelihood of the incorrect linking of the first data record and second data record, wherein the first false positive penalty is generated after the first set of results are obtained, the first false positive penalty is associated with the comparison of the first data record and generating the first positive penalty comprises determining the first false positive penalty utilizing the first set of result; and adjusting a first overall weight for a comparison between the first data record and the second data record using the first false positive penalty, wherein the first overall weight was determined utilizing the first set of results, the first overall weight is generated before it is adjusted and the adjusted first overall weight is utilized to determine if the first data record and the second data record should be linked.

* * * * *

UNITED STATES PATENT AND TRADEMARK OFFICE
CERTIFICATE OF CORRECTION

| | | |
|---|---|---|
| PATENT NO. | : 7,698,268 B1 | Page 1 of 1 |
| APPLICATION NO. | : 11/521946 | |
| DATED | : April 13, 2010 | |
| INVENTOR(S) | : Adams et al. | |

It is certified that error appears in the above-identified patent and that said Letters Patent is hereby corrected as shown below:

Column 10, line 57, replace "was determined" with -- is determined --;
Column 11, line 32, replace "was determined" with -- is determined --;
Column 11, line 62, replace "result; and" with -- results; and --;
         line 66, replace "was determined" with -- is determined --;
Column 12, line 49, replace "an identify" with -- an identity --;
         line 51, replace "comprising a" with -- comprises a --; and
Column 14, line 1, replace "was determined" with -- is determined --.

Signed and Sealed this
Twenty-third Day of August, 2011

David J. Kappos
*Director of the United States Patent and Trademark Office*